United States Patent [19]

Shillington et al.

[11] Patent Number: 4,502,606
[45] Date of Patent: Mar. 5, 1985

[54] LOCKING CLOSURE FOR DISPOSABLE CONTAINERS

[75] Inventors: Richard A. Shillington, San Clemente; Alec Oberschmidt, Leucadio, both of Calif.

[73] Assignee: Med-Safe Systems, Inc., Leucadia, Calif.

[21] Appl. No.: 533,608

[22] Filed: Sep. 19, 1983

[51] Int. Cl.³ .............................................. B65D 41/18
[52] U.S. Cl. .................................... 215/274; 215/307; 215/321; 220/229
[58] Field of Search ..................... 220/229, 306, 375; 215/321, 274, 306, 307, 320, 317

[56] References Cited

U.S. PATENT DOCUMENTS

| 3,086,674 | 4/1963 | Scheuerman | 220/229 |
| 3,189,071 | 6/1965 | Balkema | 215/321 X |
| 3,216,610 | 11/1965 | Klygis | 220/306 |
| 3,315,402 | 4/1967 | Scott et al. | 220/229 X |
| 3,830,393 | 8/1974 | Schaefer | 215/321 X |
| 4,065,035 | 12/1977 | Eissler | 220/375 X |
| 4,200,196 | 4/1980 | Bashour | 215/320 X |
| 4,235,349 | 11/1980 | Uhlig | 220/306 X |
| 4,284,200 | 8/1981 | Bush et al. | 215/321 X |
| 4,328,904 | 5/1982 | Iverson | 220/229 X |

FOREIGN PATENT DOCUMENTS

| 1183893 | 2/1959 | France | 215/307 |
| 1486483 | 5/1967 | France | 215/307 |
| 2040268 | 8/1980 | United Kingdom | 220/229 |

Primary Examiner—Donald F. Norton
Attorney, Agent, or Firm—Baker, Maxham, Callan & Jester

[57] ABSTRACT

A locking closure for disposable containers includes an annular wall structure defining a container opening and including a radially outwardly extending annular locking ridge with a closure defined by a generally flat circular disc having an axially extending peripheral skirt with an inwardly extending annular locking ridge for forceably extending over and lockingly engaging the outwardly extending annular locking ridge.

9 Claims, 5 Drawing Figures

LOCKING CLOSURE FOR DISPOSABLE CONTAINERS

BACKGROUND OF THE INVENTION

The present invention relates generally to closure structure and pertains particularly to permanent closure structure for disposable containers.

Many items that are disposed of from hospitals and the like must be disposed of in a manner so that such items can not be pilfered through access to the contents of disposing containers and the like. Such disposable items include sharp objects such as needles, syringes and cutting blades and the like which are typically disposed of in a container and the container subsequently disposed of. Many attempts have been made in the past to develop secure containers for receiving such articles and securing them from pilferage and the like. Most prior art attempts to provide such containers have been complicated and expensive.

Therefore it is desirable that a simple, inexpensive and effective disposable container and locking means therefor be available.

SUMMARY AND OBJECTS OF THE INVENTION

It is therefore the primary object of the present invention to provide a secure closure for disposable containers. In accordance with the primary aspect of the present invention, a closure for a disposable container includes peripheral wall means defining a container opening with a radially extending locking ridge disposed about the outer periphery of the wall and a cooperating closure defined by a generally flat circular disc having a axially extending skirt with an inwardly extending peripheral locking ridge for cooperative interlocking with the radially outwardly extending peripheral locking ridge. The peripheral wall includes an outer diameter extending outward beyond the outer diameter of the closure skirt for thereby shielding the edge of the peripheral skirt.

BRIEF DESCRIPTION OF THE DRAWINGS

The above and other objects and advantages of the present invention will become apparent from the following description when read in conjunction with the drawings wherein.

DETAILED DESCRIPTION OF THE PEFERRED EMBODIMENT

Figure 1:
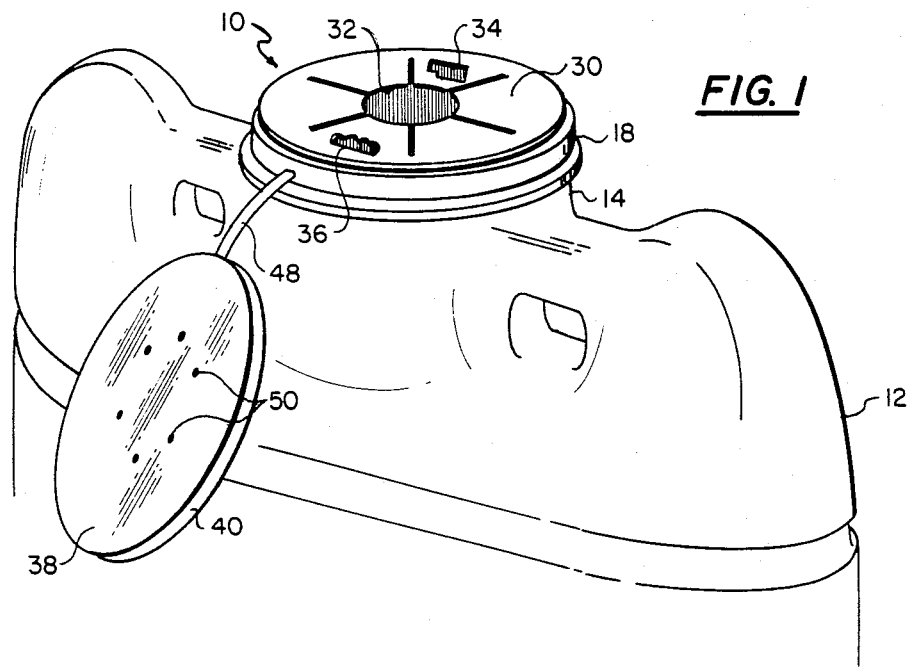
FIG. 1 is a perspective view of a portion of a container showing an opening and a closure in accordance with the invention.
Figure 2:
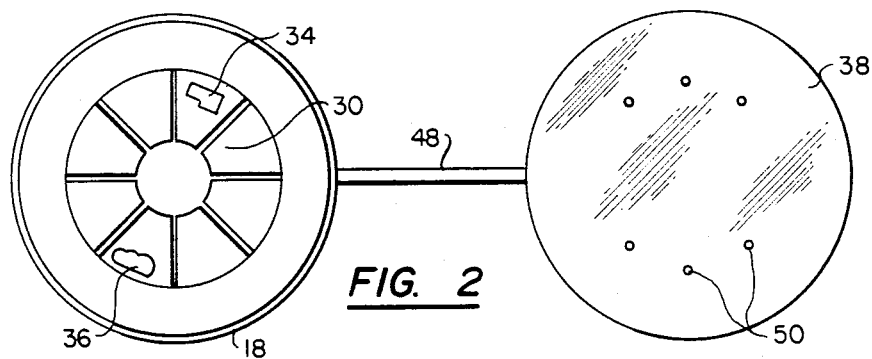
FIG. 2 is a top plan view of the closure assembly of FIG. 1.

Referring to FIG. 1 of the drawings, a closure structure designated generally by the numeral 10 is shown in position mounted on a disposable container 12. The container 12 is preferably of the general configuration and construction of that disclosed and claimed in our copending application Ser. No. 362,875, filed Mar. 24, 1982, now U.S. Pat. No. 4,454,944 entitled, "One Way Sharps Receptacle". Such structures are preferably of a moldable plastic material such as polypropylene providing a lightweight high-strength container for the disposal of sharp objects. The material can preferably withstand sterlizing temperatures of about 325 degrees Fahrenheit so that the containers can be passed through a sterlizer.

Figure 4:
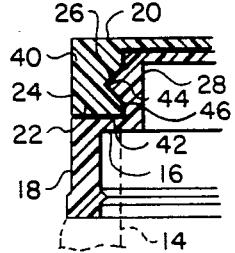
FIG. 4 is an enlarged, side elevation view in section of a portion of the closure of FIG. 3 showing details of construction.
Figure 3:
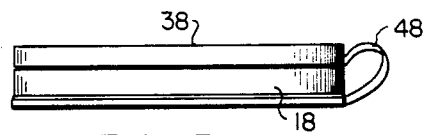
FIG. 3 is a side elevation view of the closure of FIG. 1 in the closed position.

The container preferably includes an outwardly extending generally tubular neck portion 14 which itself may form the fixed portion of the locking closure structure of the present invention. However, in the preferred embodiment the neck terminates in a tubular section 14 as shown in FIG. 4 which includes an abutting peripheral or annular shoulder 16.

The locking closure structure of the present invention includes annular wall structure defining a generally tubular neck forming a sleeve-like structure having an overlapping tubular portion 18 for fitting over the end of the tubular neck 14 of the container. The tubular neck or wall structure is fixed in place on the container such as by bonding or molding in place and includes a stepped outer surface comprising first annular surface 20 having a first diameter less than a second peripheral or cylindrical surface 22 having a second diameter between which is formed a radially extending shoulder 24. A radially extending generally V-shaped or triangular shaped cross section annular peripheral locking ridge 26 extends around the inner diameter portion of the closure structure for cooperative engagement with a locking groove of a closure member as will be described. The wall structure further defines a generally circular opening 28 with a pass-through closure structure formed by a plurality of inwardly extending generally pie-shaped flat segments 30 which are formed integral with and extending inward from the peripheral wall structure.

The annular closure and wall structure is preferably molded from a high impact but yieldable plastic material such as polypropylene, polyurethane, polyethylene or the like. The structure should be yieldable under substantial force but not easily stretchable. In most instances the container and closure structure are preferably made of a plastic material that can withstand sterlizing temperatures of on the order of about 325 degrees Fahrenheit. The pass-through closure portion is designed to permit articles to be easily inserted into the container yet discourage the insertion and removal of a hand or the like. It will be appreciated that the flaps form an inner diameter 32 which is preferably less than that of a small child's hand such that should the hand be extended into the opening the flaps will bend downward into the opening such that the removal of the hand would require forcing against the flaps thereby discouraging the attempted removal of objects from the container. Additional features of the pass-through closure include wrench type structures 34 and 36 for engaging and removal of certain type or styles of needles from syringes and the like. The shapes of the two wrench structures 34 and 36 are well known and will be readily recognized by those in the trade.

The closure member of the locking closure structure comprises a generally flat circular disc 38 having a downwardly or axially extending peripheral skirt 40 which terminates in a radial abutting face 42 adapted to tightly engage the opposing face 24 of the annular wall structure. The outer diameter of the skirt 40 is substantially the same or less than that of the outer diameter of the annular wall structure skirt portion 18.

The skirt portion 40 is formed with a generally v-shaped groove 44 which is shaped to receive the peripheral radially outwardly extending locking ridge 26. The groove 44 additionally forms below it a generally radially inwardly extending locking ridge 46 which has an inner diameter that is less than the outer diameter of the radially outwardly extending locking ridge 26.

The closure member 38 and the wall structure 18 are preferably molded simultaneously of a common material and include a tethering strap 48 molded therewith. The opening portion of the closure member 38 extends in the downward direction such that it must be consciously manipulated by twisting the strap 48 so that the closure member will be properly placed over the closure opening. By this construction it cannot be unconsciously closed simply by pivoting it directly over and slapping it down on the opening.

In operation when it is desired to lock the closure in the secured position, the closure cover 38 is manipulated around such that the downwardly depending skirt 40 faces downward over the container opening and the closure is then forced downward forcing the closure to expand outward with the skirt portions 46 being forced outward over the radially extending locking ridge 26 of the neck whereupon the lid or closure snaps into its locked position with the locking ridge 26 securely extending into the groove 44. The opposing faces 24 and 42 are adapted to fit in tight engagement thereby eliminating any space therebetween to enable extension of a fingernail, a knife blade or similar object for attempting to pry the cover from the container opening. The outer diameter or surface of the skirt portion 40 of the lid or closure 38 is equal to or less than the diameter of surface 22 such that it does not present a shoulder for engagement by a finger or an opening object or the like.

The lid or closure 38 is provided with a plurality of openings 50 for enabling steam injection or the injection of steam into the container for sterilization of the contents thereof. Similarly, it enables the escape of gas therefrom should the containers be heat shrunk to reduce the bulk thereof for disposal.

Figure 5:
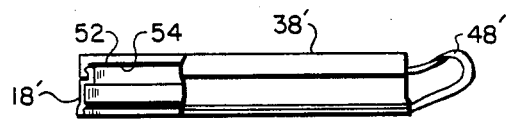
FIG. 5 is a view like FIG. 3 of an alternate embodiment of the closure structure.

Referring to FIG. 5, a slightly different embodiment is illustrated wherein annular wall structure 18' is provided with an inwardly extending pass-through opening formed by a inwardly extending portion 52 forming a pass-through opening 54 that omits the closure flap 30 as in the previous embodiment. This modifies the largest opening of a container to a somewhat smaller opening but eliminate the smaller opening formed by the flaps. Such construction may be desirable in uses where the tighter security of the previous embodiment is not required.

While we have illustrated and described our invention by means of specific embodiments, it is to be understood therein without departing from the spirit and scope of the invention as defined in the appended claims.

We claim:

1. A permanent locking closure structure for a container, comprising:
   annular wall structure defining an opening for a container, said wall structure having a stepped outer diameter defining a generally tubular neck, and end portion defining a circular opening and having a first outer diameter, an adjacent sleeve portion defining a second outer diameter greater than said first diameter, and a radial annular shoulder separating said end portion and said sleeve portion, said end portion including a radially outwardly extending annular locking ridge,
   a non-removable closure defined by a generally flat circular disk having an axially extending peripheral skirt, a radially inwardly extending annular locking ridge on the interior of said skirt for forceably enaging over said outwardly extending annular locking ridge, said skirt having a radial annular face for tight engagement with said shoulder, and an outer diameter equal to or less than said second outer diameter.

2. The locking closure structure of claim 1 wherein said skirt includes an annular groove formed on the inner surface thereof defining said inwardly extending annular locking ridge and for receiving said outwardly extending annular locking ridge and said annular groove has a generally V configuration.

3. The locking closure structure of claim 2 wherein said outwardly extending annular locking ridge has a generally triangular cross-sectional configuration.

4. The clocking closure structure of claim 1 wherein said annular wall structure includes means defining a pass-through closure structure.

5. The locking closure structure of claim 4 wherein said pass-through closure structure includes inwardly extending generally pie-shaped flaps.

6. The closure structure of claim 4 further comprising wrench means formed in said pass-through closure structure for removal of needles and the like.

7. The closure structure of claim 1 comprising:
   orienting strap means securing said closure to said wall structure and orienting said closure for non-closing engagement with said wall structure so that said strap requires twisting for orienting said closure for closing engagement with said wall structure.

8. A permanent locking closure structure for a container having a circular opening, comprising:
   annular tubular neck structure having a generally stepped outer diameter defining a circular opening, said annular tubular structure having a first diameter end portion defining said opening and a second portion having a second outer diameter greater than said first diameter with a radial annular shoulder separating said end portion from said second portion,
   a radial outwardly extending annular locking ridge formed on said first end portion on the outer diameter thereof,
   a non-removable closure defined by a generally flat circular disk having an axially extending peripheral skirt with a radially inwardly extending annular locking ridge on the interior of said skirt for forceably engaging over said outwardly extending annular locking ridge, said skirt having radial annular face for tight engagement with said shoulder, and an outer diameter equal to or less than the diameter of said second outer diameter portion,
   an orienting strap means securing said closure to said wall structure in a non-closure orientation for non-closing engagement with said structure, and
   pass-through closure structure comprising a plurality of radially inwardly extending generally pie-shaped flaps formed on said end portion for extending across said opening, said pass through closure structure defining a first mode for passing articles to said opening into a container of which said structure is mounted and said non-removeable closure defining a second mode for permanent closure of said opening.

9. The closure structure of claim 8 further comprising wrench means formed in said pass-through closure structure for engagement by and removal of needles and the like.

* * * * *